United States Patent
Cervin

(10) Patent No.: US 10,415,074 B2
(45) Date of Patent: Sep. 17, 2019

(54) SELECTIVE DETECTION OF LACTIC ACID AND/OR ACETIC ACID BACTERIA OR OF FUNGI

(71) Applicant: Charles Cervin, Commercy (FR)

(72) Inventor: Charles Cervin, Commercy (FR)

(73) Assignee: Charles Cervin, Commercy (FR)

( * ) Notice: Subject to any disclaimer, the term of this patent is extended or adjusted under 35 U.S.C. 154(b) by 0 days.

(21) Appl. No.: 15/731,735

(22) PCT Filed: Jan. 25, 2016

(86) PCT No.: PCT/FR2016/000011
§ 371 (c)(1),
(2) Date: Jul. 24, 2017

(87) PCT Pub. No.: WO2016/120534
PCT Pub. Date: Aug. 4, 2016

(65) Prior Publication Data
US 2018/0037923 A1    Feb. 8, 2018

(30) Foreign Application Priority Data

Jan. 28, 2015 (FR) ..................... 15 00163

(51) Int. Cl.

| | | |
|---|---|---|
| *C12Q 1/00* | (2006.01) | |
| *C12N 1/00* | (2006.01) | |
| *C12Q 1/20* | (2006.01) | |
| *C12Q 1/04* | (2006.01) | |
| *C12Q 1/66* | (2006.01) | |
| *G01N 21/76* | (2006.01) | |
| *G01N 33/14* | (2006.01) | |

(52) U.S. Cl.
CPC ............... *C12Q 1/008* (2013.01); *C12Q 1/04* (2013.01); *C12Q 1/66* (2013.01); *G01N 21/763* (2013.01); *G01N 33/14* (2013.01); *C12Q 2304/60* (2013.01)

(58) Field of Classification Search
CPC .......... A61K 35/66; A61K 39/00; A61K 39/02
USPC .................... 435/243, 252.4, 254.1
See application file for complete search history.

(56) References Cited

FOREIGN PATENT DOCUMENTS

| EP | 0781851 A2 | 7/1997 |
|---|---|---|
| GB | 02177419 | 1/1987 |

OTHER PUBLICATIONS

Toshihiro Takahashi, et al: "A New Rapid Technique for Detection of Microorganism . . . " Journal of Bioscience and Bioengineering, vol. 89, No. 5, Aug. 15, 2000, pp. 509-513).
Takahashi, t, et al. "Application of a bioluminescence method for the beer industry: . . . " Japan Society for Bioscence Biotechnology, and Agrochem.V 6, N. 5, May 1, 2000 p. 1032-1037.

*Primary Examiner* — Rodney P Swartz
(74) *Attorney, Agent, or Firm* — Jonathan E. Grant; Grant Patent Services

(57) ABSTRACT

A method for detecting lactic acid and/or acetic acid bacteria in a food-processing matrix is taught, using microbial flora including a lactic acid and/or acetic acid bacterial flora and a fungal flora. The bacterial flora contains an adenosine triphosphate of bacterial origin, and the fungal flora contains an adenosine triphosphate of fungal origin. The method comprises applying, to the matrix, before a first time limit, an antifungal having an antifungal action which is lethal, on the fungal flora, and at a second time limit, an antibiotic action which is non lethal, at a second time limit after the first time limit, on the bacterial flora. The microbial flora is detected between the first time limit and the second time limit; the lethal antifungal action releases, into the matrix, for the first time limit, adenosine triphosphate of fungal origin and in which the microbial flora is detected between the first time limit and the second time limit.

10 Claims, No Drawings

SELECTIVE DETECTION OF LACTIC ACID AND/OR ACETIC ACID BACTERIA OR OF FUNGI

The present application relates to the selective detection of bacteria or the selective detection of fungi in a mixture of these bacteria and of these fungi.

The present application thus relates to the detection, the measurement or the assessment of the presence of lactic acid or acetic acid bacteria in a mixture comprising these lactic acid bacteria or these acetic acid bacteria and comprising fungi, in particular yeasts or molds. Such a mixture is found in beverages such as beer, wine, in the sugar industry during pressing of sugar beet or sugar cane juice, and in carbonated sweet drinks such as lemonade, or in fruit juices during their processing.

The present application also relates to the detection, measurement or assessment of the presence of fungi in a mixture comprising lactic acid bacteria or acetic acid bacteria and comprising said fungi, in particular yeasts or molds.

The present application relates even more particularly to the assessment, in a medium containing fungi, of the presence of lactic acid or acetic acid bacteria, by measuring the adenosine triphosphate or ATP of these bacteria, or ATPmetry, in particular by making use of luciferin, luciferase and a bioluminescence measurement.

The present application also relates to said assessment by the addition of a luminescence reagent, such as luminol or a viability label, enabling the viable microorganisms to emit a measurable or detectable luminescence, with or without excitation, by any optical means.

An acetic acid bacteria refers below to an aerobic Gram-negative bacteria able to transform ethanol into acetic acid. Acetic acid bacteria are present in wine and cider and rarely in beer saturated with carbon dioxide. The development of acetic acid bacteria is undesirable in wine after alcoholic and or malolactic fermentation, as well as in beer, and in carbonated and sweet drinks.

A lactic acid bacteria refers below to a Gram-positive bacteria, facultative anaerobic or microaerophilic, which takes in particular the shape of cocci or rods or tetrads and able to ferment sugars into lactic acid. Lactic acid bacteria are present in wine, cider, sugar beet and sugar cane juices and may be found in carbonated drinks, in particular sodas and sweet juice drinks. The development of lactic acid bacteria is undesirable after wine fermentation and sulfiting, and in cider without malolactic fermentation, because they can alter the organoleptic qualities of wine and cider. Lactic acid bacteria are undesirable in beer, except for some type of Iambic beers or Berliner Weisse where lactic acid bacteria are added during the fermentation phase. In the sugar industry, the development of certain lactic acid bacteria, such as *leuconostoc mesenteroides*, are consuming sucrose in sugar beet juices, generating filtration problems and financial losses.

The words "lactic acid bacteria or acetic acid bacteria" is to be understood throughout the application as meaning either lactic acid bacteria, either acetic acid bacteria, either lactic acid bacteria and acetic acid bacteria.

The terms "bacteria" or "bacterial flora" are to be understood in the application as synonyms of "lactic acid or acetic acid bacteria", unless otherwise specified.

The terms "fungi" or "fungal flora" are to be understood in the application as synonyms of "molds or yeasts".

The term "matrix" is to be understood in the application as a composition of matter which comprises bacteria and fungi. Such a mixture may be solid, in particular when it is dry as a filtrate or after centrifugation, or wet if it is dispersed into a liquid, or gas, for example an air sampling.

The terms "food-processing matrix" are to be understood as a solid or liquid or gaseous medium containing, in volume or at its surface, a microbial flora encountered in the agri-food industry including agriculture, or during artisanal production of food or drinks.

The words "liquid phase application of a product A on a product B" are meaning in the application, an operation resulting in a liquid containing A and B in solution or in dispersion. An application in aqueous phase means a liquid phase application for a liquid which is water or a liquid compatible with bacteria survival in the obtained solution by the application.

The words ATP or adenosine triphosphate refer in the application, to the molecule which, in the biochemistry of all known living organisms, provides by hydrolysis, the energy required for the chemical reactions of metabolism.

The words "free ATP" refer to ATP outside of any cell, whether this ATP is available or not for a bioluminescence reaction.

The word luminescence refers to any luminescence not naturally occurring in the analyzed sample, but induced by the addition of one or more reagents essential to this luminescence reaction, said luminescence being detectable in viable microbial cells of the sample, in particular by any optical system with or without excitation of this luminescence.

The word "bactericide" refers to a treatment having the effect of reducing a bacterial population by at least three decimal logarithms of colony forming units/ml on an agar plate count of a sample after treatment.

Ergosterol refers to a component of the membrane or cell wall of fungi.

A "sterol precursor of ergosterol" refers to a molecule having the chemical structure of a sterol, namely a lipid possessing a sterane nucleus carrying a hydroxyl group at the C-3 position, produced during ergosterol biosynthesis in the fungal cell.

The words "beta-glucans" refer to polysaccharides consisting of D-glucose bound with beta links which may be $\beta$-1,3 links, $\beta$-1,4 or $\beta$-1,6 links, numbers indicating the atoms of D-glucose concerned.

The words "non-competitive inhibition" refer to an inhibition of an enzyme, which reduces the activity of this enzyme by binding itself with as much affinity for this enzyme, whether this enzyme is or not bound to its substrate.

The word MRS refers to either De Man, Rogosa and Sharpe broth or agar.

The word Luminol refers to a molecule whose chemical formulation C8H7N3O2 produces a chemiluminescence with a characteristic blue glow when mixed with certain oxidizers. This luminescence reaction with luminol can also be catalyzed by addition of a catalyst, such as menadione. A certain number of studies are showing a correlation between the luminescence signal of luminol and the number of bacterial cells in the sample.

The words viability label refer to any label used, either to assess the cell wall state of dead cells, damaged cells or cells with cell wall integrity, such as propidium iodide or ethidium bromide, either to detect intracellular enzymatic activity such as for example the esterase activity of a viable microbial cell often measured by introducing a non-luminescent molecule which becomes luminescent after enzymatic conversion in the viable cell, either to simultaneously assess the cell wall integrity and the intracellular enzymatic activity of the viable cell. The labeling is non-specific to a particular species of microorganisms and does not include neither nucleic probes nor DNA or RNA primers. This viability label is detectable by luminescence. It can be used with a label blocker to improve the detection by luminescence of the labeled cells.

The prior art is acquainted with the technique of ATPmetry which allows a measurement of free ATP in a solution to evaluate the biomass present in the solution. This technique supposes firstly to make the biomass ATP available by release into the solution, for example by a lysis agent which causes the death of the living organisms and releases their ATP into the solution, and then supposes to perform a luminescence measurement proportional to the amount of free ATP in the solution. For this purpose, a known bioluminescence reaction using the luciferin-luciferase substrate-enzyme complex is used. The bioluminescence reaction takes place by prior activation of the luciferin by adenosine triphosphate hydrolysis. The produced light intensity can be made proportional to the amount of free ATP in the mixture and it is thus possible, by means of a luminometer, to optically obtain an evaluation of the ATP quantity in a sample.

Lysis agent will be understood as a product able to break open bacteria or fungi membranes. However, most lysis agents give only access to the total amount of intracellular ATP of the total biomass present in a solution.

For a mixture of bacteria and fungi, it is thus impossible to obtain separately a measurement of the intracellular ATP value of the bacterial flora or a measurement of the intracellular ATP value of the fungal flora.

Mechanical filtration is then used to retain fungi when they are of larger size than bacteria. However, for a mixture of lactic acid and acetic acid bacteria, filtration is not effective. Indeed, there exist an overlap between the sizes of yeasts and fungi and the sizes of clusters of lactic acid and acetic acid bacteria, of which certain lactic acid bacteria form naturally chains of very variable lengths, tetrads, or clusters as well for acetic acid bacteria than for lactic acid bacteria. *Brettanomyces bruxellensis* yeasts present in wine and cider exposed to sulfite are, for example, reducing their size, approaching those of single-cell acetic acid and lactic acid bacteria. Some lactic acid bacteria also bind to yeasts making their mechanical separation impossible.

In practice, selective measurement by ATPmetry of lactic acid or acetic acid bacterial biomass in a mixture of a bacterial flora and of a fungal flora is therefore a difficult problem for the prior art. The same applies to obtaining the selective measurement of the fungal biomass in such a mixture, except by neglecting the bacterial biomass.

In this context, the invention relates to a method for the detection of lactic acid bacteria and/or acetic acid bacteria in an food-processing matrix comprising a microbial flora, the microbial flora comprising a lactic acid and/or acetic acid bacterial flora and comprising a fungal flora, the bacterial flora containing an adenosine triphosphate of bacterial origin, the fungal flora containing an adenosine triphosphate of fungal origin, which comprises the following steps:

applying, to the matrix, an antifungal having an antifungal action which is lethal, at a first time limit, on the fungal flora, and an antibiotic action which is non-lethal at a second time limit after the first time limit, on the bacterial flora, detecting the microbial flora between the first time limit and the second time limit; in which the lethal antifungal action releases, into the matrix, for the first time limit, adenosine triphosphate of fungal origin and the microbial flora is detected between the first time limit and the second time limit by means of the following steps:

removing the free adenosine triphosphate from the matrix then, applying to the matrix a lysis agent to release from the matrix the adenosine triphosphate of bacterial origin then, measuring the adenosine triphosphate released.

In variants of the method:

the antifungal is an inhibitor of ergosterol.

the antifungal is an inhibitor of a sterol precursor of ergosterol.

the antifungal has a glutarimide functional group and is an inhibitor of the translocation step of the elongation phase of the protein synthesis of eukaryotes.

the inhibitor of ergosterol is a molecule of the family of polyenes.

the inhibitor of a sterol precursor of ergosterol is a molecule of the family of morpholines.

the inhibitor of a sterol precursor of ergosterol is a molecule of the family of azoles.

the antifungal is an inhibitor of the synthesis of beta-glucans.

The invention also relates to a device which comprises an antifungal having, after application, an antifungal activity that is lethal, at a first time limit, on a fungal flora, and a non-lethal antibiotic activity, at a second time limit after the first time limit, on a lactic acid and/or acetic acid bacterial flora, and which comprises means for detecting a microbial flora comprising the fungal flora and the lactic acid and/or acetic acid bacterial flora.

In a variant of the device:

the means for detecting the microbial flora comprises a lysis agent.

The invention also relates to an application of the above method to the separate assessment of adenosine triphosphate of fungal origin and of adenosine triphosphate of bacterial origin in a food-processing matrix comprising a lactic acid and/or acetic acid bacterial flora and a fungal flora, comprising the following steps:

taking a first aliquot of the matrix;

taking a second aliquot of the matrix;

applying said method to the first aliquot to obtain a first measurement representative of the amount of adenosine triphosphate of bacterial origin in the matrix;

applying a lysis agent to the second sample, then measuring the free adenosine triphosphate in the second aliquot to obtain a second measurement representative of the amount of adenosine triphosphate of bacterial and fungal origin in the matrix;

forming the difference between the second measurement and the first measurement to obtain a third measurement representative of the amount of adenosine triphosphate of fungal origin in the matrix.

The invention also relates to a method for the detection of fungi in an food-processing matrix comprising a microbial flora, the microbial flora comprising a lactic acid and/or acetic acid bacterial flora and comprising a fungal flora, the bacterial flora containing an adenosine triphosphate of bacterial origin, the fungal flora containing an adenosine triphosphate of fungal origin, which comprises the following steps:

applying, to the matrix, an antifungal having an antifungal action which is lethal, at a first time limit, on the fungal flora, and an antibiotic action which is non-lethal at a second time limit after the first time limit, on the bacterial flora, measuring the adenosine triphosphate released in the matrix between the first time limit and the second time limit.

The invention will appear more clearly in the light of the embodiments described below.

In a first embodiment, an antifungal of the family of polyenes is selected, the antifungal being:

Molecule A1=Amphotericin B

This family of polyenes targets ergosterol of the membrane of fungi. The family of polyenes comprises in particular amphotericin B, nystatin, natamycin.

The toxicity results on yeasts and on bacteria are presented in the table below displaying the duration of exposure of the fungal flora to molecule A1 and the associated fluorescence measurement: yeasts lysis after exposure to the antifungal was confirmed by microscopic examination and methylene blue staining.

The words "contact time" refer to below, the time of exposure of the microorganisms to the fungicidal product, here molecule A1.

Below: "Sacch." is the abbreviation for "*Saccharomyces*".

Below: "No CFU" is the abbreviation for "No Colony forming unit on agar plate count".

| Molecule A1 dosage: 400 mg/L (milligram/Liter) contact time 4 hours | | |
|---|---|---|
| | Agar plate count contact time 0 h | Agar plate count contact time 4 h |
| Yeasts | | |
| *Sacch. Cerevisae* DSM 70449 | $8.10^4$ CFU/mL | No CFU |
| *Sacch. Cerevisae* Saflager S23 | $9.10^4$ CFU/mL | No CFU |
| *Sacch. Diastaticus* IFBM | $2.10^5$ CFU/mL | No CFU |
| *Brettanomyces bruxellensis* Wyeast labs | $3.10^5$ CFU/mL | No CFU |
| *Dekkera anomala* IFBM | $1.10^5$ CFU/mL | No CFU |
| *Zyggosaccharomyces bailii* | $3.10^5$ CFU/mL | No CFU |
| Lactic acid bacteria | | |
| *Lactobacillus brevis* IFBM | $7.10^5$ CFU/mL | $3.10^5$ CFU/mL |
| *Lactobacillus lindneri* DSM 20690 | $6.10^5$ CFU/mL | $7.10^4$ CFU/mL |
| *Lactobacillus paracasei* IFBM | $1.4.10^7$ CFU/mL | $1.10^7$ CFU/mL |
| *Lactobacillus parabuchneri* DSM 5708 | $1.4.10^6$ CFU/mL | $3.10^5$ CFU/mL |
| *Pedicoccus damnosus* IFBM | $1.1.10^5$ CFU/mL | $2.10^7$ CFU/mL |
| *Oenococcus oeni* DSM 20252 | $4.10^7$ CFU/mL | $5.10^7$ CFU/mL |
| Acetic acid bacteria | | |
| *G. oxydans* DSM 7145 | $8.10^7$ CFU/mL | $9.10^7$ CFU/mL |
| *Acetobacter aceti* DSM 3508 | $2.9.10^7$ CFU/mL | $3.10^7$ CFU/mL |

It can be seen that for molecule A1 of the family of polyenes used, an antifungal was found which administered at doses of 400 mg/liter remains non-bactericidal.

| Molecule A1: Dosage: 200 mg/L contact time 4 hours | | |
|---|---|---|
| | Agar plate count contact time 0 h | Agar plate count contact time 4 h |
| Yeasts | | |
| *Brettanomyces bruxellensis* Wyeast labs | $6.10^6$ CFU/mL | No CFU |
| Lactic acid bacteria | | |
| *Lactobacillus brevis* IFBM | $7.10^5$ CFU/mL | $2.9.10^5$ CFU/mL |
| *L. lindneri* DSM 20690 | $6.10^6$ CFU/mL | $2.10^6$ CFU/mL |
| *L. paracasei* IFBM | $1.4.10^7$ CFU/mL | $2.4.10^7$ CFU/mL |
| *L. parabuchneri* DSM 5708 | $1.4.10^6$ CFU/mL | $1.10^6$ CFU/mL |
| *Pedicoccus damnosus* IFBM | $7.2.10^5$ CFU/mL | $8.10^5$ CFU/mL |
| *Oenococcus oeni* DSM 20252 | $4.10^9$ CFU/mL | $6.10^9$ CFU/mL |
| Acetic acid bacteria | | |
| *G. oxydans* DSM 7145 | $8.10^8$ CFU/mL | $1.10^9$ CFU/mL |
| *Acetobacter aceti* DSM 3508 | $2.9.10^7$ CFU/mL | $8.10^8$ CFU/mL |

It can be seen that for molecule A1 of the family of polyenes used, an antifungal was found which administered at doses of 200 mg/liter remains non-bactericidal for lactic acid bacteria and acetic acid bacteria.

It is estimated that for the molecule A1 the concentration threshold allowing to obtain the effect of the invention of being non-bactericidal for the lactic acid and acetic acid bacteria while being antifungal for the yeast populations is comprised within 50 mg/l or 50 mg/l and 100 mg/l.

In order to determine whether a particular molecule is suitable for the invention, a person skilled in the art may constitute a first list of antifungal products and a second list of non-bactericidal products for bacteria and select the products appearing in the first and second list for which the fungicidal activity intervenes prior to the bactericidal activity. However, an experimental verification of the fungicidal activity will be necessary to determine the minimum antifungal concentration per mg/L or in microgram per milliliter depending on the targeted fungal flora.

In order to utilize the molecule A1 selectivity property towards bacteria and fungi, mentioned above, it is then processed as mentioned below.

First an initial mixture of lactic acid and/or acetic acid bacteria and a fungal flora representative of a wine flora during wine aging phase following sulfiting is prepared, which is inoculated into an artificial wine or a mixture of lactic acid bacteria and a fungal flora which is inoculated into a pasteurized beer in its bottle, and constituting an artificial aqueous solution.

Or else, a sample is sampled from a filtered or unfiltered beer, having turbidity and/or bitterness, usually caused by lactic acid bacteria, or from a wine during wine aging phase following sulfiting, or following bottling and filtration but having undergone an alteration of its organoleptic qualities such as bitterness or an oily character in the mouth, or a bouquet with a slight vinegar odor, usually caused by lactic acid or acetic acid bacteria. The application of the method is then carried out during the post sulfiting wine aging phase to monitor the abnormal growth of lactic acid and acetic acid bacteria whose number must gradually decrease following the various racking operations, or in the brewery during the alcoholic fermentation phase of brewery worts, after and before beer filtration, for the monitoring of undesirable lactic acid bacteria growth for quality control purposes.

In a first step, the initial mixture is exposed to an antifungal, in this case A1, at a concentration, for example of 100 mg/l, by application into an aqueous phase, for example, for 8 hours.

To carry out this application into an aqueous phase: if the antifungal and the initial mixture are each of them in an aqueous phase, they will be mixed; if only one of the two is in powder form, it will be mixed into the aqueous phase of the other, and if both are in powder form, they may be mixed with an aqueous buffer.

Following exposure of the initial mixture to the antifungal, the fungal cells have released their ATP into the aqueous phase and it is possible to eliminate this fungal ATP from the aqueous phase by various known means (filtration, ATPase, . . . ).

Bacteria are the only viable microorganisms remaining at this stage and they are larger in size than ATP molecules, which allows for example a filtration.

The method of the invention can therefore, after eliminating the fungal ATP, use any counting method of the remaining bacteria, provided that this method is unaffected by the presence in the aqueous phase, of membranes debris of dead fungal cells.

Any counting method of live bacteria (for instance culture and enumeration by solid-phase or by flow cytometry, impedancemetry, bended flow cytometry, in english "fountain flow cytometry", also viability label, luminol, luminescence reagent, . . . ) could thus be used in an equivalent manner to the measurement on dead bacteria described now.

To count the bacteria, a measurement of their bacterial ATP will be used below.

It is thus possible to filter the aqueous phase by means of a filter with a pore diameter in the order of 0.2 micron or 0.45 micron, that is to say a larger size than ATP molecules but at a lower size than the size of bacteria, to obtain a filtration residue on the filter containing dead fungal cell membranes lacking ATP and live bacteria containing ATP.

ATP may also be eliminated by an enzyme such as ATPase which removes free ATP, any means for removing free ATP in the aqueous phase at this stage is an equivalent means for the invention.

As a method of choice, for the counting of bacteria, a method combining total lysis and ATPmetry will then be used with the invention. For this purpose, cells will be killed by exposure to a lysis agent in liquid phase, usually aqueous, but above all capable of releasing ATP from the cells, their survival being no longer useful at this stage. Other liquids than water are therefore conceivable for this application of a lysis agent, provided that these liquids do not substantially inhibit the enzymatic reaction of ATP bioluminescence.

The liquid-phase application of the lysis agent being, for example, non-specific for bacteria, it will cause lysis of all microbial cells present in the aqueous phase, therefore a priori of the lactic acid and acetic acid bacterial cells predominantly present in the initial mixture, by releasing their bacterial ATP into the liquid phase. If other bacteria are present, they will constitute a systematic error and the invention is thus applicable especially to beverages in the fermentation phase (in particular beer, wine, cider) in which the presence of other bacteria than lactic acid and acetic acid bacteria is weakly conceivable, due to these beverage pH or the presence of carbon dioxide in beer.

At this stage where the ATP of bacteria constitutes mainly the free ATP in the aqueous phase of the method of the invention, it is then possible to use, in an equivalent manner, any quantification method of free ATP in the solution, and in particular ATPmetry.

For this purpose, the coupled luciferin/luciferase and the bioluminescence reaction with ATP of this coupling will be conveniently used, to optically determine the bacterial ATP and to derive an estimate of the biomass of bacterial origin in the initial mixture.

For the molecule A1, an Atpmetry check of the fungal flora destruction and of the antifungal treatment harmlesness on the lactic acid or acetic acid bacterial flora has been done for a contact time of 4 hours or 8 hours and on different strains.

Strains tested: *Oenococcus oeni* DSM, *Gluconobacter oxydans, B. bruxellensis, S. cerevisae*, prepared in MRS broth.

1 ml of sample is sampled and mixed with 9 ml of fungicidal treatment prepared in aqueous solution, of which 500 µL is then analyzed.

Materials: Lum-1 ATP meter (model analogous to Profile-1 bioluminometer from New Horizons Diagnostics) was tested with Biothema Ab bioluminescence reagents, namely reagents "ATP Eliminating Buffer", "Extractant B/S", "ATP Reagent HS" and 0.45 µm porosity Filtravette™ cuvette-filters from New Horizons Diagnostics.

Description of the Initial Protocol:

Addition of 500 µL of the suspension without fungicidal treatment or with fungicidal treatment inside a 10 mL plastic syringe containing at its end a cell concentrator incorporating a Filtravette™.

Filtration through the Filtravette™

Filtravette™ deposit on a Filtravette™ holder with a blotter pad below

Addition of 50 µL of "ATP Eliminating Buffer" inside the Filtravette 10 minutes incubation at room temperature Flushing of the "ATP Eliminating Buffer" Reagent through the blotter pad by positive pressure Addition of 30 µL of "Extractant B/S". Homogenization and 1 minute incubation.

Addition of 240 µL of "ATP Reagent HS". Homogenization.

Insertion of the Filtravette into the Lum-1 drawer and closure of the drawer.

125 seconds after closing the Lum-1 drawer, recording of the displayed value (in RLU, Relative Light Unit)

| Atp bioluminescence without antifungal treatment and with antifungal treatment | | | |
|---|---|---|---|
| *Oenococccus oeni* DSM | $0.9.10^7$ CFU/500 µL without antifungal | | $4.10^6$ CFU/500 µL with antifungal 4 h contact time |
| RLU | 42766 | 175354 | 104893  72542 |
| *Gluconobacter oxydans* | $1.10^7$ CFU/500 µL | | $4.1.10^6$ CFU/500 µL |
| RLU | 115966 | | 62074  77057 |
| *Brettanomyces bruxellensis* | $2.8.10^6$ CFU/500 µL without antifungal | | 0 CFU/500 µL with antifungal 4 h contact time |
| RLU | >1000000 | No test | 584  170 |
| *Saccharomyces cerevisae* DSM | $5.10^3$ CFU/500 µL | | Antifungal 4 h contact time no count on agar plate count |
| RLU | >1000000 | >1000000 | 4665 |
| *Saccharomyces cerevisae* DSM | $5.10^2$ CFU/500 µL | | Antifungal 4 h contact time no count on agar plate count |
| RLU | 206949 | 149508 | 642 |

For the molecule A1 the strains were also tested: *B. bruxellensis*, *S. diastaticus*, prepared in a solution of Ringer Lactate.

Simplified Protocol:

1 ml of sample is sampled and mixed with 9 ml of fungicidal treatment prepared in aqueous solution, of which 100 μL is then analyzed Use of 300 milliliters transparent Greiner Bio One sterile flat bottom disposable cuvettes with Biothema AB bioluminescence reagents 1. Addition of 100 μL of the suspension to be tested into the cuvette already in place in the reading chamber of the device.
2. If necessary, addition of 30 μL of "Extractant B/S" then homogenization.
3. Addition of 150 μL of "ATP Reagent HS", Homogenization.
4. Light emission reading (in RLU, Relative Light Unit) 65 seconds after bioluminometer drawer slide closure.

*Brettanomyces bruxellensis* before and after antifungal treatment. Atp bioluminescence following addition of luciferine/luciferase

| backgroud noise in duplicate without lysis agent with luciferin/luciferase | total bioluminescence in duplicate with lysis agent | total bioluminescence with lysis agent |
|---|---|---|
| Concentration | | |
| $2.7.10^3$ CFU/100 μL Untreated | $2.7.10^3$ CFU/100 μL Untreated | 0 CFU/100 μL Treated 8 h antifungal contact time |
| Bioluminescence values in Relative Light Units (RLU) | | |
| 5346    5390 | 242958    265513 | 4441    4433 |
| Concentration | | |
| $2.7.10^2$ CFU/100 μL Untreated | $2.7.10^2$ CFU/100 μL Untreated | 0 CFU/100 μL Treated 8 h antifungal contact time |
| Bioluminescence values in Relative Light Units (RLU) | | |
| 862    718 | 26990    31661 | 933    553 |

Bioluminescence values before and after treatment demonstrate treatment efficiency

*Saccharomyces diastaticus* before and after fungicidal treatment. Atp bioluminescence following addition of luciferin-luciferase

| luminescent background noise in duplicate without lysis agent with luciferin/luciferase | total bioluminescence in duplicate with lysis agent | luminescent background noise in duplicate without lysis agent after luciferin/luciferase addition | total bioluminescence in duplicate with lysis agent |
|---|---|---|---|
| Concentration | | | |
| $7.5.10^2$ CFU/100 μL Untreated | $7.5.10^2$ CFU/100 μL Untreated + extractant | 0 CFU/100 μL Treated (4 h) | 0 CFU/100 μL Treated (4 h) |
| Bioluminescence values in Relative Light Units (RLU) | | | |
| 211    223 | 16239    16707 | 3803    3837 | 4393 |
| Concentration | | | |
| $7.5.10^1$ CFU/100 μL Untreated | $7.5.10^1$ CFU/100 μL Untreated + extractant | 0 CFU/100 μL Treated (4 h) | 0 CFU/100 μL Treated (4 h) |
| Bioluminescence values in Relative Light Units (RLU) | | | |
| 34    34 | 1934    1241 | 457    436 | 482 |

Bioluminescence values before and after treatment demonstrate treatment efficiency The above method is applicable with all the embodiments of the invention, that is, with any antifungal selective for lactic acid or acetic acid bacteria.

Likewise, in all embodiments of the invention, it will be possible to use on two aliquots, that is to say two samples of the same quantity of the initial mixture supposed to be homogeneous, the method below in order to determine selectively the fungal biomass in the initial mixture:

the above method on the first aliquot to obtain a first measurement of the value of the bacterial biomass lysing the second aliquot to release fungal and bacterial ATP Measuring fungal ATP by ATPmetry, to obtain a second measurement of the value of fungal and bacterial biomass Subtracting the first measurement from the second measurement to obtain a third measurement of the value of the fungal biomass alone.

The molecule A1 is therefore adapted to the invention

In a second embodiment, an antifungal of the family of morpholines is selected, the antifungal being:

Molecule A2=Amorolfine

This family of morpholines targets a sterol precursor of ergosterol of the membrane of fungi The toxicity results on yeasts and on bacteria are presented in the table below displaying the duration of exposure of the fungal flora to the molecule A2 and are obtained by enumeration on MRS agar media.

| Molecule A2 Dosage: 400 mg/L 4 hours contact time | | |
|---|---|---|
| | Agar plate count Contact time 0 h | Agar plate count Contact time 4 h |
| Yeasts | | |
| *Sacch. Cerevisae* DSM 70449 | $5.8.10^5$ CFU/mL | No CFU |
| *Sacch. Cerevisae* Saflager S23 | $3.2.10^5$ CFU/mL | No CFU |
| *Sacch. Diastaticus* IFBM | $2.10^6$ CFU/mL | No CFU |

-continued

Molecule A2
Dosage: 400 mg/L 4 hours contact time

|  | Agar plate count Contact time 0 h | Agar plate count Contact time 4 h |
|---|---|---|
| *Brettanomyces bruxellensis* Wyeast labs | $1.8.10^6$ CFU/mL | No CFU |
| *Dekkera anomala* IFBM | $5.10^3$ CFU/mL | No CFU |
| *Zyggosaccharomyces bailii* | $2.2.10^6$ CFU/mL | No CFU |
| Lactic acid bacteria | | |
| *Lactobacillus brevis* IFBM | $7.10^5$ CFU/mL | $8.10^5$ CFU/mL |
| *L. lindneri* DSM 20690 | $6.10^5$ CFU/mL | $5.10^5$ CFU/mL |
| *L. paracasei* IFBM | $1.4.10^7$ CFU/mL | $4.10^7$ CFU/mL |
| *L. parabuchneri* DSM 5708 | $1.4.10^6$ CFU/mL | $3.10^4$ CFU/mL |
| *Pedicoccus damnosus* IFBM | $1.1.10^5$ CFU/mL | $1.10^4$ CFU/mL |
| *Oenococcus oeni* DSM 20252 | $4.10^7$ CFU/mL | $5.10^7$ CFU/mL |
| Acetic acid bacteria | | |
| *G. oxydans* DSM 7145 | $8.10^7$ CFU/mL | $9.10^7$ CFU/mL |
| *Acetobacter aceti* DSM 3508 | $2.9.10^7$ CFU/mL | $9.10^6$ CFU/mL |

It can be seen that for the molecule A2 of the family of morpholines used, an antifungal was found which administered at doses of 400 mg/liter is neither bactericidal for the lactic acid flora nor bactericidal for the acetic acid flora.

Molecule A2: Dosage: 200 mg/L contact time 4 hours

|  | Agar plate count contact time 0 h | Agar plate count contact time 4 h |
|---|---|---|
| Yeasts | | |
| *Brettanomyces bruxellensis* Wyeast labs | $6.10^6$ CFU/mL | No CFU |
| Lactic acid bacteria | | |
| *Lactobacillus brevis* IFBM | $7.10^5$ CFU/mL | $1.10^6$ CFU/mL |
| *L. lindneri* DSM 20690 | $6.10^6$ CFU/mL | $1.10^6$ CFU/mL |
| *L. paracasei* IFBM | $1.4.10^7$ CFU/mL | $5.10^7$ CFU/mL |
| *L. parabuchneri* DSM 5708 | $1.4.10^6$ CFU/mL | $5.10^5$ CFU/mL |
| *Pedicoccus damnosus* IFBM | $7.2.10^5$ CFU/mL | $1.5.10^5$ CFU/mL |
| *Oenococcus oeni* DSM 20252 | $4.10^9$ CFU/mL | $6.10^9$ CFU/mL |
| Acetic acid bacteria | | |
| *G. oxydans* DSM 7145 | $8.10^8$ CFU/mL | $1.10^9$ CFU/mL |
| *Acetobacter aceti* DSM 3508 | $2.9.10^7$ CFU/mL | $6.10^6$ CFU/mL |

It can be seen also that for the molecule A2 of the family of morpholines used, an antifungal was found which administered at doses of 200 mg/liter is neither bactericidal for the lactic acid flora nor bactericidal for the acetic acid flora and is therefore adapted to the invention.

It is estimated that for the molecule A2 the concentration threshold allowing to obtain the effect of the invention of being non-bactericidal for the lactic acid and acetic acid bacteria while being earlier antifungal for the yeast populations, is comprised within 100 mg/l and 200 mg/l.

The same methods as in the first embodiment are applicable to determine the bacterial or fungal biomass.

In a third embodiment, an antifungal of the family of azoles is selected, the antifungal being:

Molecule A3=voriconazole.

This family of azoles targets a sterol precursor of ergosterol of the membrane of fungi.

The toxicity results on yeasts and on bacteria are presented in the table below displaying the duration of exposure of the fungal flora to the molecule A3.

Molecule A3
Dosage: 400 mg/L contact time 18 hours

|  | Agar plate count contact time 0 h | Agar plate count contact time 18 h |
|---|---|---|
| Yeasts | | |
| *Sacch. Diastaticus* IFBM | $1.10^4$ CFU/mL | No CFU |
| *Brettanomyces bruxellensis* Wyeast labs | $8.10^4$ CFU/mL | No CFU |
| *Dekkera anomala* IFBM | $7.10^5$ CFU/mL | No CFU |
| Lactic acid bacteria | | |
| *Lactobacillus brevis* IFBM | $7.10^5$ CFU/mL | $1.10^6$ CFU/mL |
| *L. lindneri* DSM 20690 | $6.10^5$ CFU/mL | $7.10^4$ CFU/mL |
| *L. paracasei* IFBM | $1.4.10^7$ CFU/mL | $2.10^7$ CFU/mL |
| *L. parabuchneri* DSM 5708 | $1.4.10^6$ CFU/mL | $6.10^5$ CFU/mL |
| *Pedicoccus damnosus* IFBM | $1.1.10^5$ CFU/mL | $2.10^4$ CFU/mL |
| *Oenococcus oeni* DSM 20252 | $4.10^7$ CFU/mL | $1.10^8$ CFU/mL |
| Acetic acid bacteria | | |
| *G. oxydans* DSM 7145 | $8.10^7$ CFU/mL | $1.10^8$ CFU/mL |
| *Acetobacter aceti* DSM 3508 | $2.9.10^7$ CFU/mL | $4.10^7$ CFU/mL |

It can be seen that for the molecule A3 of the family of azoles used, an antifungal was found which administered at doses of 400 mg/liter is neither bactericidal for the lactic acid flora nor bactericidal for the acetic acid flora.

The molecule A3 is therefore adapted to the invention at a concentration of 400 mg/L.

Molecule A3: Dosage: 200 mg/L contact time 18 hours

|  | Agar plate count contact time 0 h | Agar plate count contact time 18 h |
|---|---|---|
| Yeasts | | |
| *Brettanomyces bruxellensis* Wyeast labs | $6.10^6$ CFU/mL | $9.10^1$ CFU/mL |
| Lactic acid bacteria | | |
| *Lactobacillus brevis* IFBM | $7.10^5$ CFU/mL | $1.10^6$ CFU/mL |
| *L. lindneri* DSM 20690 | $6.10^6$ CFU/mL | $1.10^6$ CFU/mL |
| *L. paracasei* IFBM | $1.4.10^7$ CFU/mL | $5.10^7$ CFU/mL |
| *L. parabuchneri* DSM 5708 | $1.4.10^6$ CFU/mL | $5.10^5$ CFU/mL |
| *Pedicoccus damnosus* IFBM | $7.2.10^5$ CFU/mL | $1.5.10^5$ CFU/mL |
| *Oenococcus oeni* DSM 20252 | $4.10^9$ CFU/mL | $6.10^9$ CFU/mL |
| Acetic acid bacteria | | |
| *G. oxydans* DSM 7145 | $8.10^8$ CFU/mL | $1.10^9$ CFU/mL |
| *Acetobacter aceti* DSM 3508 | $2.9.10^7$ CFU/mL | $6.10^6$ CFU/mL |

It can be seen that for the molecule A3 of the family of azoles used, an antifungal was found which administered at doses of 200 mg/liter is neither bactericidal for the lactic acid flora nor bactericidal for the acetic acid flora.

It is estimated that for the molecule A3 the concentration threshold allowing to obtain the effect of the invention is comprised within 200 mg/l and 300 mg/l.

The same methods as in the first embodiment are applicable to determine the bacterial or fungal biomass.

The molecule A3 is therefore adapted to the invention at a concentration of 200 mg/L.

In a fourth embodiment, an antifungal which has a glutarimide functional group and is an inhibitor of the translocation step of the elongation phase of the protein synthesis of eukaryotes is selected, the antifungal being:

Molecule A4=cycloheximide

This family also includes in particular the following compound: lactimidomycin.

The results of toxicity on yeasts and on bacteria are presented in the table below displaying the duration of exposure of the fungal flora to the molecule A4.

| Molecule A4 Test N° 2: 400 mg/L | | |
|---|---|---|
| | Agar plate count contact time 0 h | Agar plate count contact time 18 h |
| Yeasts | | |
| Sacch. Cerevisae DSM 70449 | $5.10^4$ CFU/mL | No CFU |
| Sacch. Diastaticus IFBM | $4.10^4$ CFU/mL | No CFU |
| Brettanomyces bruxellensis Wyeast labs | $7.3.10^5$ CFU/mL | No CFU |
| Dekkera anomala IFBM | $1.10^5$ CFU/mL | $1.2.10^1$ CFU/mL |
| Lactic acid bacteria | | |
| Lactobacillus brevis IFBM | $7.10^5$ CFU/mL | $2.10^6$ CFU/mL |
| L. lindneri DSM 20690 | $6.10^5$ CFU/mL | $1.10^5$ CFU/mL |
| L. paracasei IFBM | $1.4.10^7$ CFU/mL | $3.10^7$ CFU/mL |
| L. parabuchneri DSM 5708 | $1.4.10^6$ CFU/mL | $6.10^6$ CFU/mL |
| Pedicoccus damnosus IFBM | $1.1.10^5$ CFU/mL | $4.10^4$ CFU/mL |
| Oenococcus oeni DSM 20252 | $4.10^7$ CFU/mL | $1.10^8$ CFU/mL |
| Lactic acid bacteria | | |
| G. oxydans DSM 7145 | $8.10^7$ CFU/mL | $1.10^8$ CFU/mL |
| Acetobacter aceti DSM 3508 | $2.9.10^7$ CFU/mL | $9.10^7$ CFU/mL |

It can be seen that for the molecule A4 used, of the above functionally defined family, an antifungal was found which administered at doses of 400 mg/liter or more, nevertheless preserves bacteria cell integrity.

It is estimated that for the molecule A4 the concentration threshold allowing to obtain the effect of the invention is greater than 300 mg/l.

The same methods as in the first embodiment are applicable to determine the bacterial or fungal biomass.

The molecule A4 is adapted to the invention.

The molecule A4 is particularly suitable to wine during the wine aging phase after sulfiting, targeting wild yeasts present in and in the vicinity of lees.

In a fifth embodiment, an antifungal of the family of echinocandins, inhibitors of the synthesis of beta-glucans of fungal cells, the antifungal being:

Molecule A5=caspofungin

This family of compounds inhibits the synthesis of beta-glucans of the fungal cell by a non-competitive inhibition of the 1,3-Beta-glucan synthase enzyme and comprises at least the following compounds: pneumocandins, echinocandin B, cilofungin, caspofungin (or in french "caspofongine" or "casponfungine"), micafungin (or in french "micafongine" or "micafungine"), anidulafungin (or in french "anidulafongine" or "anidulafungine").

The toxicity results on yeasts and on bacteria are presented in the table below displaying the duration of exposure of the fungal flora to the molecule A5:

| Molecule A5 dosage: 400 mg/L contact time 4 hours | | |
|---|---|---|
| | Agar plate count contact time 0 h | Agar plate count contact time 4 h |
| Yeasts | | |
| Sacch. Cerevisae DSM 70449 | $2.10^5$ CFU/mL | No CFU |
| Sacch. Cerevisae Saflager S23 | $3.10^5$ CFU/mL | No CFU |
| Sacch. Diastaticus IFBM | $4.10^4$ CFU/mL | No CFU |
| Brettanomyces bruxellensis Wyeast labs | $1.7.10^4$ CFU/mL | No CFU |
| Dekkera anomala IFBM | $1.4.10^4$ CFU/mL | No CFU |
| Zyggosaccharomyces bailii | $2.10^5$ CFU/mL | No CFU |
| Lactic acid bacteria | | |
| Lactobacillus brevis IFBM | $7.10^5$ CFU/mL | $2.10^2$ CFU/mL |
| L. lindneri DSM 20690 | $6.10^5$ CFU/mL | $1.10^2$ CFU/mL |
| L. paracasei IFBM | $1.4.10^7$ CFU/mL | $1.10^2$ CFU/mL |
| L. parabuchneri DSM 5708 | $1.4.10^6$ CFU/mL | No CFU |
| Pedicoccus damnosus IFBM | $1.1.10^5$ CFU/mL | No CFU |
| Oenococcus oeni DSM 20252 | $4.10^7$ CFU/mL | $5.10^7$ CFU/mL |
| Acetic acid bacteria | | |
| G. oxydans DSM 7145 | $8.10^7$ CFU/mL | $9.10^7$ CFU/mL |
| Acetobacter aceti DSM 3508 | $2.9.10^7$ CFU/mL | $2.10^6$ CFU/mL |

It can be seen that for the molecule A5 of the family of echinocandins used, an antifungal was found which administered at doses of 400 mg/liter remains non-bactericidal for the acetic acid bacteria and for the lactic acid bacteria *Oenococcus oeni*.

| Molecule A5 Dosage: 200 mg/L contact time time 4 hours | | |
|---|---|---|
| | Agar plate count contact time 0 hour | Agar plate count contact time 4 h |
| Yeasts | | |
| Brettanomyces bruxellensis Wyeast labs | $6.10^6$ CFU/mL | No CFU |
| Lactic acid bacteria | | |
| Lactobacillus brevis IFBM | $7.10^5$ CFU/mL | $1.10^2$ CFU/mL |
| L. lindneri DSM 20690 | $6.10^6$ CFU/mL | $9.10^1$ CFU/mL |
| L. paracasei IFBM | $1.4.10^7$ CFU/mL | $1.1.10^4$ CFU/mL |
| L. parabuchneri DSM 5708 | $1.4.10^6$ CFU/mL | No CFU |
| Pediococcus damnosus IFBM | $7.2.10^5$ CFU/mL | No CFU |
| Oenococcus oeni DSM 20252 | $4.10^9$ CFU/mL | $6.10^9$ CFU/mL |
| Acetic acid bacteria | | |
| G. oxydans DSM 7145 | $8.10^8$ CFU/mL | $1.10^9$ CFU/mL |
| Acetobacter aceti DSM 3508 | $2.9.10^7$ CFU/mL | $1.10^5$ CFU/mL |

It can be seen that for the molecule A5 of the family of echinocandins used, an antifungal was found which administered at doses of 200 mg/liter remains non-bactericidal for the acetic acid bacteria and for the lactic acid bacteria *Oenococcus oeni*.

It is estimated that for the molecule A5 the concentration threshold allowing to obtain the effect of the invention to be non-bactericidal for the acetic acid bacteria while being antifungal for the yeast populations is between 100 mg/l and 200 mg/l.

The invention therefore allows, by applying certain antifungals to a beverage or a juice containing a lactic acid and/or acetic acid flora and containing fungi, to measure the bacterial biomass reliably and independently from the fungal biomass. The invention also allows to determine the fungal biomass by subtracting the bacterial biomass from the total biomass.

The invention thus allows in a simple manner, at the accuracy of the measurement of bacterial ATP performed or at the accuracy of any counting method of bacteria used in replacement of ATPmetry applied to the remaining bacteria, following application of the non-bactericidal antifungal, to detect or to estimate the value of the bacterial biomass in a mixture of a fungal flora and of a lactic acid and/or acetic bacterial flora.

To this end, a person skilled in the art may search for a fungal membrane component, such as mannans or chitins, among the antifungal inhibitors of this component or of one of its precursors on the biosynthesis path of said component, as follows:

The selection may generally involve an inhibitor of a biosynthesis reaction specific to the fungus kingdom, that is to say on a branch of the biosynthesis pathway of the component. In the case of the ergosterol component for the *Saccharomyces cerevisiae* biosynthesis pathway, selection is thus made on the specific branch starting from lanosterol. Members of the family of Allylamines, for example, are not part of the inhibitors of the sterol precursors of ergosterol biosynthesis. A molecule of this family was thus tested without a yeasticidal nor bactericidal effect being observed in less than twenty-four hours contact time.

The selection may involve any other luminescence reagent, such as the use of luminol, or any cell viability label, rendered detectable by any optical means.

In general terms, the invention also relates, for its teaching and the definition of "antifungal product having a bactericidal action posterior to a lethal antifungal action", to an inhibitor of a biosynthesis reaction of a component of the fungal membrane, that is to say that this inhibitor inhibits a reaction occurring in the biosynthesis pathway of the component.

The invention is in particular susceptible of industrial application in the making of wine, beer, cider, sodas and carbonated beverages and in the production of sugar from sugar beet juice or sugar cane juice.

It is also seen that the invention can be applied in all its embodiments in the form of a method for the selective detection of fungi in an food-processing matrix comprising a microbial flora, the microbial flora comprising a lactic acid and/or acetic acid bacterial flora and comprising a fungal flora, the bacterial flora containing an adenosine triphosphate of bacterial origin, the fungal flora containing an adenosine triphosphate of fungal origin, by respecting the following steps: applying to the matrix an antifungal having a lethal antifungal action, at a first time limit, on the fungal flora, and a non lethal antibiotic action at a second time limit after the first time limit, on the bacterial flora, said lethal action releasing the adenosine triphosphate of fungal origin for the first time limit; measuring between the first time limit and the second time limit, the adenosine triphosphate of fungal origin released into the matrix. Particularly by ATPmetry.

Indeed, as soon as an antifungal according to the invention is identified and has a first lethal action on a fungal flora and a second action posterior to the first action on a bacterial flora, it can be used for selective measurement of bacteria in a mixture of these two flora by measuring, in particular by ATPmetry, the ATP of the remaining bacteria following the lethal action or the fungal ATP, in a time window during which fungi are dead and bacteria are alive.

The invention claimed is:

1. A method for the detection of lactic acid bacteria and/or acetic acid bacteria in a carbonated or fermented beverage consisting of a lactic acid and/or acetic acid bacterial flora as well as a fungal flora, said method comprising:
    a) applying, to the carbonated or fermented beverage, an antifungal having an antifungal action which is lethal, at a first time limit, on the fungal flora, and an antibiotic action which is non-lethal on the lactic acid and/or acetic acid bacterial flora up to a second time limit;
    b) detecting the microbial flora between the first time limit and the second time limit, during which the lethal antifungal action releases, into the carbonated or fermented beverage, for the first time limit, adenosine triphosphate of fungal origin and in which the microbial flora is detected between the first time limit and the second time limit by:
        i) removing the free adenosine triphosphate from the carbonated or fermented beverage;
        ii) applying to the carbonated or fermented beverage a lysis agent, to release from the carbonated or fermented beverage the adenosine triphosphate of bacterial origin; and
        iii) measuring the adenosine triphosphate released wherein the detection of adenosine triphosphate is indicative of the presence of bacteria selected from the group consisting of lactic acid bacteria, acetic bacteria and combinations thereof in said carbonated or fermented beverage.

2. The method according to claim 1 wherein the antifungal is inhibitor of ergosterol.

3. The method according to claim 1 wherein the antifungal is an inhibitor of a sterol precursor of said ergosterol.

4. The method according to claim 1 wherein the antifungal has a glutarimide functional group and is an inhibitor of the translocation step of the elongation phase of the protein synthesis of eukaryotes.

5. The method according to claim 1 wherein the antifungal is an inhibitor of the synthesis of beta-glucans.

6. The method according to claim 2 wherein the inhibitor of said ergosterol is a molecule of the family of polyenes.

7. The method according to claim 3, wherein the inhibitor of the sterol precursor of said ergosterol is a molecule of the family of morpholines.

8. The method according to claim 3, wherein the inhibitor of the sterol precursor of said ergosterol is a molecule of the family of azoles.

9. The method according to claim 1 to the separate assessment of adenosine triphosphate of fungal origin and of adenosine triphosphate of bacterial origin in the carbonated or fermented beverage consisting of a lactic acid and/or acetic acid bacterial flora and a fungal flora, comprising:
    a) obtaining a sample of a first aliquot of the carbonated or fermented beverage;
    b) obtaining a sample of a second aliquot of the carbonated or fermented beverage;
    c) applying said method according to claim 1 to the first aliquot to obtain a first measurement representative of the amount of adenosine triphosphate of lactic acid and/or acetic acid bacterial origin in the carbonated or fermented beverage;
    d) applying a lysis agent to the second sample, then measuring the free adenosine triphosphate in the second aliquot to obtain a second measurement representative of the amount of adenosine triphosphate of bacterial and fungal origin in the carbonated or fermented beverage; and e) forming the difference between the second measurement and the first measurement to obtain a third measurement representative of the amount of adenosine triphosphate of fungal origin in the carbonated or fermented beverage.

10. A method for the detection of fungi in a carbonated or fermented beverage containing a microbial flora consisting of a lactic acid and/or acetic acid bacterial flora as well as a fungal flora comprising applying, to the carbonated or fermented beverage, an antifungal having an antifungal action which has:

i) a lethal action, at a first time limit, on the fungal flora, said lethal action releasing adenosine triphosphate of fungal origin at the first time limit, and ii) an antibiotic action which is non-lethal on the bacterial flora up to a second time limit; and b) measuring, between the first time limit and the second time limit, the adenosine triphosphate of fungal origin released in the carbonated or fermented beverage, wherein the adenosine triphosphate released at said first time limit is indicative of the presence of fungi in said carbonated or fermented beverage.

* * * * *